United States Patent [19]

Höfgen et al.

[11] Patent Number: 5,723,463
[45] Date of Patent: Mar. 3, 1998

[54] PYRIDO [3,2-E]PYRAZINONES WITH ANTI-ASTHMATIC ACTION AND PROCESSES FOR THEIR MANUFACTURE

[75] Inventors: Norbert Höfgen, Dresden; Thomas Büchner, Bonn; Ute Achterrath-Tuckermann, Maintal; Stefan Szelenyi, Schwaig; Bernhard Kutscher, Maintal, all of Germany

[73] Assignee: ASTA Medica Aktiengesellschaft, Dresden, Germany

[21] Appl. No.: 621,315

[22] Filed: Mar. 25, 1996

[30] Foreign Application Priority Data

Mar. 24, 1995 [DE] Germany .................. 195 10 965.1

[51] Int. Cl.$^6$ .................. C07D 241/00; A61K 31/495
[52] U.S. Cl. .................. 514/250; 544/346
[58] Field of Search .................. 544/346; 514/250

[56] References Cited

U.S. PATENT DOCUMENTS

| | | | |
|---|---|---|---|
| 5,055,465 | 10/1991 | Davey | 514/212 |
| 5,153,196 | 10/1992 | McQuaid et al. | 514/250 |
| 5,166,344 | 11/1992 | Davey | 514/212 |
| 5,405,847 | 4/1995 | Dieter et al. | 514/212 |
| 5,473,073 | 12/1995 | Albaugh et al. | 544/346 |
| 5,532,236 | 7/1996 | Jacobsen et al. | 514/228.5 |
| 5,541,324 | 7/1996 | Ten Brink et al. | 544/346 |

FOREIGN PATENT DOCUMENTS

| | | |
|---|---|---|
| 2112290 | 10/1994 | Canada . |
| 43 29 970 A1 | 10/1994 | Denmark . |
| 0 400 583 | 12/1990 | European Pat. Off. . |
| 0 584 487 A2 | 3/1994 | European Pat. Off. . |
| 623 620 A1 | 4/1994 | European Pat. Off. . |
| WO 93/20077 | 10/1993 | Japan . |
| 06128261 A | 5/1994 | Japan . |
| 06128262 A | 5/1994 | Japan . |
| 94/2246 | 3/1994 | South Africa . |
| 94/2964 | 4/1994 | South Africa . |

OTHER PUBLICATIONS

Davey et al., "Novel Compounds Possessing Potent cAMP and cGMP Phosphodiesterase Inhibitory ... and Their Aza Analogues", *J. Med. Chem.*, 1991, 34:2671–2677.

Derwent Abstract No. 94–343271/43 re EP dated Nov. 1994.

Derwent Abstract No. 94–311439/39 re DE 4329970 dated Oct. 1994.

Nagarajan et al., Condensed Heterotricycles: Pyrrolo [1,2-α]quinoxaline Derivatives, Indian Journal of Chemistry, vol. 10, Apr. 1972, pp. 344–350.

*Primary Examiner*—Matthew V. Grumbling
*Attorney, Agent, or Firm*—Cushman Darby & Cushman IP Group of Pillsbury Madison & Sutro LLP

[57] ABSTRACT

The invention relates to novel pyrido[3,2-e]pyrazinones, processes for their preparation and their pharmaceutical use.

The compounds have anti-asthmatic and anti-allergic effects.

12 Claims, No Drawings

PYRIDO [3,2-E]PYRAZINONES WITH ANTI-ASTHMATIC ACTION AND PROCESSES FOR THEIR MANUFACTURE

BACKGROUND OF THE INVENTION

1. Field of the Invention

The invention relates to novel compounds of the formula

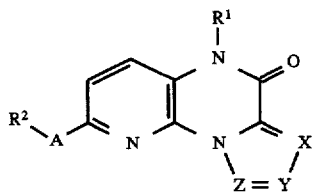

where

A either represent $CH_2$, $NR^3$ or O;

X, Y and Z stand for N or $CR^4$, where at least one of X, Y and Z must represent N.

$R^1$ can represent H (but only when A stands for $NR^3$); and $C_1$–$C_{10}$-alkyl (optionally also branched), that can be substituted once or several times with hydroxy-, $C_1$–$C_6$-alkyloxy, $C_1$–$C_6$-alkenyloxy-, $C_1$–$C_6$-alkinyloxy, aryl (optionally substituted), aryloxy (optionally substituted), heteroaryl (optionally substituted), heteroaryloxy (optionally substituted), amino, substituted amino groups, but also with halogen, $NO_2$, CN, $C=OR^5$ or $S(O)_nR^6$ (with n from 0 to 2); $C_1$–$C_{10}$-alkenyl (optionally also branched), that can be substituted once or several times with hydroxy, $C_1$–$C_6$-alkyloxy, $C_1$–$C_6$-alkenyloxy, $C_1$–$C_6$-alkinyloxy, aryl (optionally substituted), aryloxy (optionally substituted), heteroaryl (optionally substituted), heteroaryloxy (optionally substituted), amino, substituted amino groups, but also with halogen, $NO_2$, CN, $C=OR^5$ or $S(O)_nR^6$ (with n from 0 to 2); $C_1$–$C_{10}$-alkinyl (optionally also branched), that can be substituted once or several times with hydroxy, $C_1$–$C_6$-alkyloxy, $C_1$–$C_6$-alkenyloxy, $C_1$–$C_6$-alkinyloxy, aryl (optionally substituted), aryloxy (optionally substituted), heteroaryl (optionally substituted, heteroaryloxy (optionally substituted), amino, substituted amino groups, but also with halogen, $NO_2$, CN, $C=OR^5$ or $S(O)_nR^6$ (with n from 0 to 2); $C_5$–$C_7$-cycloalkyl that can be substituted once or several times with hydroxy, $C_1$–$C_6$-alkyloxy, $C_1$–$C_6$-alkenyloxy, $C_1$–$C_6$-alkinyloxy, aryl (optionally substituted), aryloxy (optionally substituted), heteroaryl (optionally substituted), heteroaryloxy (optionally substituted), amino, substituted amino groups, but also with halogen, $NO_2$, CN, $C=OR^5$ or $S(O)_nR^6$ (with n from 0 to 2).

$R^2$ can stand for H; $C_1$–$C_{10}$-alkyl (optionally also branched), that can be substituted once or several times with hydroxy, $C_1$–$C_6$-alkyloxy, $C_1$–$C_6$-alkenyloxy, $C_1$–$C_6$-alkinyloxy, aryl (optionally substituted), aryloxy (optionally substituted), heteroaryl (optionally substituted), heteroaryloxy (optionally substituted), amino, substituted amino groups, but also with halogen, $NO_2$, CN, $C=OR^5$ or $S(O)_nR^6$ (with n from 0 to 3); $C_1$–$C_{10}$-alkenyl (optionally also branched), that can be substituted once or several times with hydroxy, $C_1$–$C_6$-alkyloxy, $C_1$–$C_6$-alkenyloxy, $C_1$–$C_6$-alkinyloxy, aryl (optionally substituted), aryloxy-(optionally substituted), heteroaryl (optionally substituted), heteroaryloxy (optionally substituted), amino, substituted amino groups, but also with halogen, $NO_2$, CH, $C=OR^5$ or $S(O)_nR^6$ (with n from 0 to 2); $C_1$–$C_{10}$-alkinyl (optionally also branched) that can be substituted once or several times with hydroxy, $C_1$–$C_6$-alkyloxy, $C_1$–$C_6$-alkenyloxy, $C_1$–$C_6$-alkinyloxy, aryl (optionally substituted), aryloxy (optionally substituted), heteroaryl (optionally substituted), heteroaryloxy (optionally substituted), amino, substituted amino groups, but also with halogen, $NO_2$, CN, $C=OR^5$ or $S(O)_nR^6$ (with n from 0 to 2); $C_5$–$C_7$-cycloalkyl, that can be substituted once or several times with hydroxy, $C_1$–$C_6$-alkyloxy, $C_1$–$C_6$-alkenyloxy, $C_1$–$C_6$-alkinyloxy, aryl (optionally substituted), aryloxy (optionally substituted), heteroaryl (optionally substituted), heteroaryloxy (optionally substituted), amino, substituted amino groups, but also with halogen, $NO_2$, $C=OR^5$ or $S(O)_nR^6$ (with n from 0 to 2).

$R^3$ stands for H or $C_1$–$C_6$-alkyl.

$R^4$ represents H; $C_1$–$C_6$-alkyl (optionally branched); halogen.

$R^5$ stands for H; $C_1$–$C_6$-alkyl (optionally branched); phenyl; OH; $C_1$–$C_6$-alkyloxy (optionally branched); aryloxy (optionally substituted); amino (optionally substituted).

$R^6$ represents H; $C_1$–$C_6$-alkyl; aryl (optionally substituted); OH; $C_1$–$C_6$-alkyloxy; aryloxy (optionally substituted); amino (optionally substituted).

The invention also relates to the physiologically acceptable salts of the compounds of formula I, the processes for the preparation of the compounds of formula I and their pharmaceutical use.

2. Background Information

European patent application 0 400 583 relates to imidoquinoxalines and their aza-analogs of the general formula

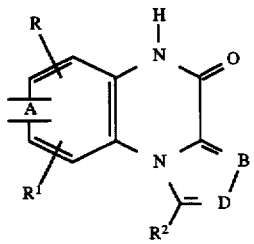

where A represent a nitrogen atom or CH, B and D a nitrogen atom or CH or a substituted carbon atom and the radicals R, $R^1$, $R^2$ represent hydrogen or various organic substituents. These compounds are said to have a positive inotropic vessel-dilating effect.

Furthermore, indian Journal of Chemistry, Volume 10, 1972, pages 344–350 describes inter alia the preparation of compounds of formula

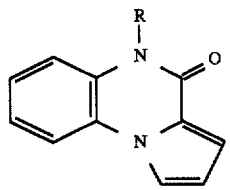

R=—$(CH_2)_nNR^1R^2$, where the radical R can be 3-dimethylaminopropyl-(1), 2-morpholinoethyl-(1), 2-pyrrolidinoethyl-(1) or 2-dimethylaminoethyl-(1). No pharmacological effect is given.

European patent application 0 584 487 relates to 4,5-dihydro-4-oxo-pyrrolo[1,2-a]-quinoxalines and their aza-analogs of general formula

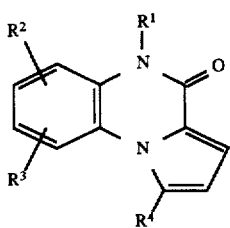

where the radicals $R^1$, $R^2R^3$ and $R^4$ stand for a plurality of organic substituents. These compounds are described as having anti-allergic, anti-asthmatic, anxiolytic, hypotensive and vasodilatory effects as well as a positive inotropic effect which are causatively based on a selective PDE III inhibition.

Patent application WO(PCT) 93 20 077 relates to imidazoquinoxalinones of general formula

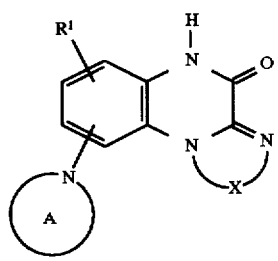

where A stands for 5-ring heterocycles with 2 or 3 nitrogen atoms in the ring, $R^1$ can be $NO_2$ or $CF_3$ and X stands for various in part nitrogen-containing chains with up to 4 chain members.

These compounds are described as glutamate receptor antagonists with psychotropic and anti-ischaemic effect.

Japanese patent application JP 06 128 261 and JP 06 128 262 relate to the preparation of compounds of general formula

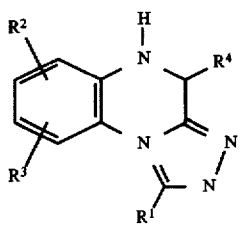

where the radicals $R^1$, $R^2$, $R^3$ and $R^4$ stand for various organic substituents. No pharmacological effect is given.

European patent application 0 623 620 relates to the preparation of compounds of general formula

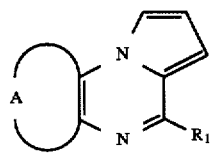

where A stands for anellated aromatic or heteroaromatic ring systems and $R_1$ for substituted amino groups. The compounds described have in part 5HT$_3$-antagonist effects.

European patent application 0 518 530 relates to the preparation of compounds of the general formulae

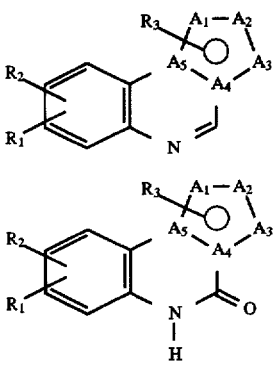

where $R_1$, $R_2$ and $R_3$ stand for various organic substituents and $A^1$ to $A_5$ for C or N, where at least two of them represent N. These compounds are antagonists of receptors of excitatory amino acids. Published German patent application DE 43 29 970 relates to the preparation of compounds of general formula

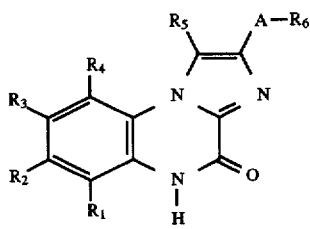

where A stands for a saturated or unsaturated alkylene group with 1–5 carbon atoms, $R_1$, $R_2$, $R_3$, $R_4$ and $R_5$ represent various organic substituents and $R_6$ stands for a functional group that contains a carbonyl group. These compounds are described as antagonists of receptors of excitatory amino acids.

SUMMARY OF THE INVENTION

The invention describes the compounds set out in the patent claims. The new compounds according to the invention are pharmacologically active and have in particular strong anti-asthmatic and anti-allergic effects on the basis of selective PDE IVN inhibition.

It is an object of the invention to provide new compounds having valuable pharmacological properties.

The invention also relates to processes for the preparation of the new compounds described in the patent claims as well as to the use thereof.

Those compounds of formula I, which contain asymmetric carbon atoms and generally occur as racemates can be separated into the optically active isomers in a manner known per se, for example with an optically active acid. It is, however, also possible from the beginning to use an optically active starting substance, a correspondingly optically active or diastereomeric compound then being obtained. Of compounds of formula I, which contain an asymmetric carbon atom, the invention therefore comprises the D-form, the L-form and D,L-mixtures as well as the diastereomeric forms in the case of several asymmetric carbon atoms. Depending on the process conditions and starting substances, the compounds of formula I can be obtained as free compounds or in the form of their salts. The salts obtained can be converted into the free bases in a manner known per se, for example with alkali or ion exchangers, or into the free acids with inorganic or organic acids. Salts can be obtained from the compounds of formula I released in this manner by reaction with inorganic or organic acids or with inorganic or organic bases that are suitable for the formation of therapeutically usable salts.

The compounds of the invention are suitable for the preparation of pharmaceutical formulations. The pharmaceutical formulations can contain one or several of the compounds of the invention. Conventional physiologically acceptable diluting agents, carriers and auxiliary substances can be used to prepare the pharmaceutical formulations or therapeutically usable forms.

In accordance with the invention compounds of formula I are prepared by reacting compounds of formula

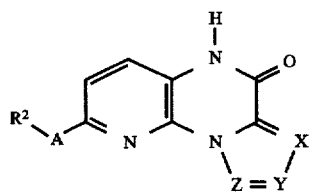

II where X, Y, Z, A and $R^2$ have the meaning given, with $R^1$ - Hal (Hal=halogen) in the presence of an inorganic or organic basic catalyst, where $R^1$ has the meaning given. The process can be carried out without solvents or in a suitable solvent or dispersing agent. Solvents or dispersing agents that can for example be considered are: aromatic hydrocarbons such as benzene, toluene, xylene, mesylene; lower aliphatic ketones such as acetone, methylethyl ketone, diethyl ketone; ethers such as diethyl ether, tetrahydrofuran, dioxan; sulfoxides such as dimethylsulfoxide; tertiary acid amides such as dimethyl formamide, dimethyl acetamide, tetramethylurea, hexamethylphosphoric acid triamide, N-methylpyrrolidone; halogenated hydrocarbons such as chlorobenzene, dichlorobenzene, carbon tetrachloride; lower alcohols such as methanol, ethanol, isopropanol as well as mixtures of the agents stated, optionally also with water. The reaction is for example carried out at temperatures between 20° and 200° C., preferably 50° to t 30° C. In the case of the starting component $R^1$ - Hal, Hal preferably represents chlorine, bromine or iodine.

The reaction is preferably carried out in the presence of acid binding agents such as alkali carbonates (sodium carbonate, potassium carbonate), alkali acetates, alkali hydroxides or tertiary basis (triethylamine, pyridine). The starling components of formula II are preferably used in the form of their metal salts. Alkali salts can be used in particular. The preparation of alkali salts is effected for example by reaction with the corresponding alkali hydrides, alkali amides, alkali alcoholates or also alkali metals in a solvent (lower alcohol, aromatic hydrocarbon, tertiary acid amides) or with aqueous alkali (for example NaOH).

In accordance of the invention, compounds of formula I are also prepared by reacting compounds of formula

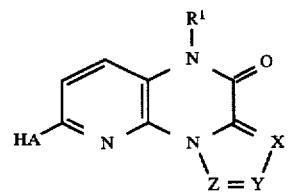

III where A, X, Y, Z and $R^1$ have the meaning given, with $R^2$-Hal (Hal=halogen) in the presence of an inorganic or organic basic catalyst, where $R^2$ has the meaning given. The process can be carried out without solvent or in a suitable solvent or dispersing agent. Solvents or dispersing agents that can, for example, be considered are: aromatic hydrocarbons such as benzene, toluene, xylene, mesitylene; lower aliphatic ketones such as acetone, methylethyl ketone, diethyl ketone; ethers such as diethyl ether, tetrahydrofuran, dioxan; sulfoxides such as dimethyl sulfoxide; tertiary acid amides such as dimethylformamide, dimethylacetamide, tetramethylurea, hexamethylphosphoric acid triamide, N-methylpyrrolidone; halogenated hydrocarbons such as chlorobenzene, dichlorobenzene, carbon tetrachloride; lower alcohols such as methanol, ethanol, isopropanol and mixtures of the agents mentioned, optionally also with water. The reaction is for example carried out at temperatures between 20° and 200° C., preferably at 50° to 130° C.

In the case of the starting component $R^2$ - Hal, Hal preferably represents chlorine, bromine or iodine.

The reaction is preferably carried out in the presence of acid-binding agents such as alkalicarbonates (sodium carbonate, potassium carbonate), alkali acetates, alkali hydroxides or tertiary bases (triethylamine, pyridine). The starting components of formula III are preferably used in the form of their metal salts. The alkali salts are particularly suitable. The preparation of the alkali salts is effected for example by reaction with the corresponding alkali hydrides, alkali amides, alkali alcoholates or also alkali metals in a solvent (lower alcohol, aromatic hydrocarbon, tertiary acid amides) or with aqueous alkali (for example NaOH).

The new pyrido[3,2-e]pyrazinones can be converted into the corresponding salts with inorganic or organic acids or bases in water or in organic solvents. The compounds of the invention of formula I and their salts are biologically active. The compounds of the invention display a strong in vitro inhibition of the phosphodiesterase isoenzyme IV and V, a strong influence of the trachea recontracted by histamine (guinea pigs) as well as good effects in in vivo asthma models, such as in the asthmatic late phase reaction (eosinosphilia) in guinea pigs.

DETAILED DESCRIPTION OF THE INVENTION

Methods

Determination of phosphodiesterase activity

Phosphodiesterase (PDE) activity is determined with a few modifications (Bauer, A. C.; Schwabe, U., An improved assay of cyclic 3',5'-nucleotide phosphodiesterase with QAE Sephadex A-25. Naunyn-Schmiedeberg's Arch. Pharmacol. 311 193–198 (1980)) after the method described by Thompson et al. (Thompson, W. J.; Appleman, M. M., Assay of cyclic nucleotide phosphodiesterase and resolution of multiple molecular forms of the enzyme. Adv. Cycl. Nucl. Res. 10 69–92 (1979)) The reaction mixture contains 40 mM Tris-HCl (pH 7.4), 5 mM $MgCl_2$, 0.5 µM cAMP or cGMP, [$^3$H]cAMP or [$^3$H]cGMP (approx. 20.000 cpm/test) and the other components needed to record the individual isoenzymes (see below). The final volume is 200 µl. Test substances are prepared as stock solutions in DMSO. The DMSO concentration in the reaction mixture is the same or less than 1% v/v. The PDE activity is not influenced at this DMSO concentration. After pre-incubation for 5 minutes at 37° C. the reaction is started by adding the substrate (cAMP or cGMP). The samples are incubated for a further 15 minutes at 37° C. The reaction is stopped by adding 50 µl 0.2N HCl. The samples remain in the ice for a further 10 minutes. After incubation with 25 µg 5'-nucleotidase (Crotalus atrox) for 10 minutes at 37° C. the samples are applied to QAE Sephadex A-25 columns (Econor columns, Bio-Rad). The columns are eluted with 2 ml 30 mM ammonium formiate (pH 6.0). The radioactivity of the individual fractions is recorded using scintigraphy.

The PDE IV (cAMP-specific) activity is determined after the method described by Schudt et al. (Schudt C.; Winter S.; Forderkurz S.; Hatzelmann A.; Ullrich V., Influence of selective phosphodiesterase inhibitors on human neutrophil functions and levels of cAMP and Ca. Naunyn-Schmiedeberg's Arch. Pharmacol. 344, 682–690 (1991)) describe a method in the cytosol of human polymorphonuclear leucocytes. The substrate is cAMP. Addition of motapizon, a specific PDE III inhibitor (1 µM) totally suppresses the PDE III activity stemming from the possible thrombolytic impurity.

PDE V (cGMP-specific) is isolated from human blood platelets (Schudt C.; Winder S.; Müller B.; Ukena D., Zardaverine as a selective inhibitor of phosphodiesterase isoenzymes. Biochem. Pharmacol. 42, 153–162 (1991)). cGMP is used as substrate.

Influence on the trachea precontracted using histamine

Guinea pigs are exsanguinated under narcosis. The trachea is then prepared free from adjacent tissue and cut into five equal parts (at least 3 trachea-rings wide). The trachea parts are suspended in a bath filled with a nutrient solution (Krebs-Henseleit). The strength of contraction of the trachea can be measured using force transducers. After suspension, a 15-minute acclimatisation period is allowed. The trachea is then totally relaxed using isoprenaline ($1\times10^{-7}$ mol/l). The bath vessel is then rinsed. A contraction maximum is triggered using metacholine ($10\times10^{-5}$ mol/l). The bath vessel is then rinsed again. Histamine ($1\times10^4$ mol/l) is then added. The contraction maximum is reached after approx. 10 minutes. The test substance is then added to the bath in increasing concentration and the contraction-triggering effect determined in percent to an untreated control. The mean contraction-triggering concentration is calculated using regression apparatuses. To check the function of the organs, isoprenaline ($1\times10^{-5}$ mol/l) is then added to the bath to see whether the organs are still able to relax.

Determination of the asthmatic late phase reaction (oesinophilia) in guinea pigs Male guinea pigs (250–300 g, Pirbright white, Charles River Wiga) are actively sensitised by s.c. injection of ovalbumin (10 µg+100 mg aluminium hydroxide) and boosted 2 weeks later. One week after the boosting (10 µg+100 mg aluminium hydroxide) the animals are exposed of an aerosol of nebulised 0.5 % ovalbumin solution for 20 seconds. 24 hours later, the bronchoalveolar lavage (BAL) is carried out using 2×5 ml sodium chloride solution on animals sacrificed with an overdose of pentobarbital. The lavage liquid is pooled and centrifuged for 10 minutes. The cell pellet is suspended in 1 ml physiological sodium chloride solution and the eosinophils are counted microscopically in a counting chamber using a Becton-Dickinson eosinophil kit. The eosinophils are counted for each guinea pig. The mean value is calculated for each group. The inhibition of the eosinophils for the group treated with substance is obtained using the formula:

(A−C)−(B−C)/(A−C)×100=% inhibition

A=Eosinophils in the untreated control group challenged with ovalbumin

B=Eosinophils in the group treated with the substance and challenged with ovalbumin C=Eosinophils in the control group not challenged with ovalbumin The substance was applied 2 hours before allergen challenge p.o. (in 1% methocel) or i.p. (in 0.5% methocel). The control groups receive 1% methocel p.o. or 0.5% methocel i.p. 2 hours before allergen challenge.

The following effects were for example obtained for the compound according to embodiment 1:

PDE IV—inhibition (in vitro): $IC_{50}=0.1$ µmol/l

PDE V—inhibition (in vitro): $IC_{50}=0.095$ µmol/l

Histamine precontracted trachea: $IC_{50}=0.7$ µmol/l

Ovalbumin-induced eosinophilia (guinea pigs): 1 mg/kg i.p. 74% inhibition.

EMBODIMENTS

Examples for the preparation of compounds of formula I from compounds of formula II:

EXAMPLE 1

1-ethyl-8-methoxy-3-methyl-5-propyloimidazo[1,5-a]pyrido[3,2-e]-pyrazinone

Variant A 10 g (0.038 mol) 1-ethyl-8-methoxy-3-methyl-imidazo[1,5-a]pyrido[3,2-e]pyrazinone are stirred into 200 ml dimethylformamide. 3 g (0.095 mol) sodium hydride (80%) are added in portions at 20° C. with stirring. After the mixture has been stirred for 2 hours, 8.5 g (0.07 mol) n-propyibromide are added dropwise within 15 minutes. The resulting solution is heated to 70°–80° C. for 2 hours with stirring and then heated for a further 8 hours to 100° C. The solvent is removed in a vacuum after cooling to 20° C. The raw product crystallising is first stirred out with 150 ml of water at about 50° C. and then recrystallised from cyclohexane.

Yield: 8.5 g (73% of theory)

Melting point: 136°–137° C.

Variant B 10 g (0.038 mol) 1-ethyl-8-methoxy-3-methyl-imidazo[1,5-a]pyrido[3,2-e]pyrazinone are stirred into 200 ml dimethylacetamide. 3 g (0.095 mol) sodium hydride (80%) are added in portions at 20° C. with stirring. After the mixture has been stirred for 2 hours 8.5 g (0.07 mol) n-propyl bromide are added dropwise within 15 minutes. The resultant solution is stirred for a further 15 hours at 20°–25° C. The solvent is then removed in a vacuum. The crystallising raw product is purified as described for variant A. Yield:

8.1 g (70% of theory)

Melting point: 135°–137° C.

Variant C 10 g (0.038 mol) 1-ethyl-8-methoxy-3-methyl-imidazo[1,5-a]pyrido[3,2-e]pyrazinone are heated to 120° C. with 6.9 g (0.05 mol) anhydrous potassium carbonate in 80 ml dimethylformamide with stirring. 8.5 g (0.07 mol) n-propyl bromide are then added dropwise within 15 minutes. The reaction mixture is stirred for 7 hours at 120°–130° C. After cooling the inorganic salts are suctioned off and the solvent removed from the filtrate in the vacuum. The mixture is recrystallised from cyclohexane to purify the crystallising raw product.

Yield: 8.0 g (69% of theory)

Melting point: 135°–137° C.

Numerous further compounds of formula I can be prepared using the variants given by way of example, the following being set out by way of example:

TABLE 1

| Example | X | Y | Z | A | R¹ | R² | Variant | Yield [%] | Melting pt. [°C.] |
|---|---|---|---|---|---|---|---|---|---|
| 2 | C—CH$_3$ | N | C—C$_2$H$_5$ | O | CH$_3$ | H | B | 92 | 276–278 Ethanol |
| 3 | C—CH$_3$ | N | C—C$_2$H$_5$ | O | C$_2$H$_5$ | H | B | 90 | 157–160 Ethanol |
| 4 | C—CH$_3$ | N | C—C$_2$H$_5$ | O | C$_3$H$_7$ | H | B | 77 | 295 Ethanol |
| 5 | C—CH$_3$ | N | C—C$_2$H$_5$ | O | CH$_3$ | CH$_3$ | B | 74 | 173 DMF |
| 6 | C—CH$_3$ | N | C—H | O | CH$_3$ | CH$_3$ | B | 76 | 254 Ethyl acetate |
| 7 | C—H | N | C—CH$_3$ | O | CH$_3$ | CH$_3$ | B | 80 | 279 DMF |
| 8 | C—CH$_3$ | N | C—C$_2$H$_5$ | O | C$_2$H$_5$ | CH$_3$ | B | 68 | 145–147 DMF |
| 9 | C—CH$_3$ | N | C—H | O | C$_2$H$_5$ | CH$_3$ | B | 67 | 177 Ethyl acetate |
| 10 | C—CH$_3$ | N | C—C$_2$H$_5$ | O | C$_4$H$_9$ | CH$_3$ | C | 54 | 99–102 Cyclohexane |
| 11 | C—CH$_3$ | N | C—C$_2$H$_5$ | O | C$_5$H$_{11}$ | CH$_3$ | A | 33 | 72–74 Cyclohexane |
| 12 | C—CH$_3$ | N | C—C$_2$H$_5$ | O | (CH$_2$)$_2$CH(CH$_3$)$_2$ | CH$_3$ | A | 11 | 113–116 Cyclohexane |
| 13 | C—CH$_3$ | N | C—C$_2$H$_5$ | O | CH$_2$C$_6$H$_5$ | CH$_3$ | B | 44 | 166–167 Acetone |
| 14 | C—CH$_3$ | N | C—C$_2$H$_5$ | O | C$_2$H$_4$C$_6$H$_5$ | CH$_3$ | C | 10 | 174–176 Acetone |
| 15 | C—CH$_3$ | N | C—C$_2$H$_5$ | O | CH$_2$C$_6$H$_4$(2-Cl) | CH$_3$ | A | 58 | 245–246 DMF |
| 16 | C—CH$_3$ | N | C—C$_2$H$_5$ | O | CH$_2$C$_6$H$_4$(4-Cl) | CH$_3$ | A | 64 | 201–202 DMF |
| 17 | C—CH$_3$ | N | C—C$_2$H$_5$ | O | CH$_2$C$_6$H$_3$(2,4-di-Cl) | CH$_3$ | C | 17 | 211–213 Acetone |
| 18 | C—CH$_3$ | N | C—C$_2$H$_5$ | O | CH$_2$C$_6$H$_3$(2,6-di-Cl) | CH$_3$ | A | 33 | 209–212 Toluene |
| 19 | C—CH$_3$ | N | C—C$_2$H$_5$ | O | CH$_2$C$_6$H$_4$(2-F) | CH$_3$ | A | 51 | 186–187 Ethanol |
| 20 | C—CH$_3$ | N | C—C$_2$H$_5$ | O | CH$_2$C$_6$H$_4$(4-F) | CH$_3$ | A | 60 | 189–191 DMF |
| 21 | C—CH$_3$ | N | C—C$_2$H$_5$ | O | CH$_2$C$_6$H$_3$(2-Cl,6-F) | CH$_3$ | A | 26 | 197–200 Acetone |
| 22 | C—CH$_3$ | N | C—C$_2$H$_5$ | O | CH$_2$C$_6$H$_4$(2-CH$_3$) | CH$_3$ | A | 50 | 240–242 Toluene |
| 23 | C—CH$_3$ | N | C—C$_2$H$_5$ | O | CH$_2$C$_6$H$_4$(4-OCH$_3$) | CH$_3$ | A | 61 | 156–158 Ethanol |
| 24 | C—CH$_3$ | N | C—C$_2$H$_5$ | O | CH$_2$C$_6$H$_2$(3,4,5-tri-OCH$_3$) | CH$_3$ | A | 69 | 191–192 Ethanol |
| 25 | C—CH$_3$ | N | C—C$_2$H$_5$ | O | CH$_2$C$_6$H$_4$(4-OCH$_2$—C$_6$H$_5$) | CH$_3$ | A | 54 | 147–149 Ethanol |
| 26 | C—CH$_3$ | N | C—C$_2$H$_5$ | O | (CH$_2$)$_3$COOC$_2$H$_5$ | CH$_3$ | B | 57 | 130–132 Isopropanol |
| 27 | C—CH$_3$ | N | C—C$_2$H$_5$ | O | (CH$_2$)$_3$COONa | CH$_3$ | B | 65 | 293–295 Ethanol |
| 28 | C—CH$_3$ | N | C—C$_2$H$_5$ | O | C$_3$H$_7$ | C$_2$H$_5$ | B | 67 | 124–126 Ethanol |
| 29 | C—CH$_3$ | N | C—C$_2$H$_5$ | O | C$_2$H$_5$ | CH$_2$COCH$_3$ | B | 70 | 174–176 Ethanol |

Examples for the preparation of compounds of formula I from compounds of formula III:

EXAMPLE 30

8-cyclopentyloxy-1-ethyl-3-methyl-5-propyl-imidazo[1,5-a]pyrido[3,2-e]-pyrazinone Variant A 3.2 g (0.11 mol) 1-ethyl-8-hydroxy-3-methyl-imidazo[1,5-a]pyrido[3,2-e]pyrazinone are stirred into 60 ml dimethylformamide. 0.9 g (0.03 mol) sodium hydride (80%) are added in portions at 20° C. After the mixture has been stirred for 2 hours 2.1 g (0.02 mol) cyclopentyl chloride are added dropwise within 15 minutes. The resulting solution is heated to 70°–80° C. with stirring for 2 hours and then heated for a further 8 hours to 100° C. After cooling to 20° C. the solvent is removed in a vacuum. The raw product that crystallises is first stirred out with 50 ml hot water at about 50° C. and then recrystallised from ethyl acetate.

Yield: 3.0 g (77% of theory)

Melting point: 138°–140° C.

Variant B 3.2 g (0.011 mol) 1-ethyl-8-hydroxy-3-methyl-imidazo[1,5-a]pyrido[3,2-e]pyrazinone are stirred into 60 ml dimethylacetamide. 0.9 g (0.03 mol) sodium hydride (80%) are added in portions at 20° C. with stirring. After the mixture has been stirred for 2 hours 2.1 g (0.02 mol) cyclopentyl chloride are added dropwise within 15 minutes. The resultant solution is stirred for a further 15 hours at 20°–25° C.

The solvent is then removed in a vacuum. Purification of the crystallising raw product is carried out as described for variant A.

Yield: 2.7 g (70% of theory)

Melting point: 138°–140° C.

Numerous further compounds of formula I can be prepared using the variants given by way of example, the following being set out by way of example:

TABLE 2

| Example | X | Y | Z | A | R¹ | R² | Variant | Yield [%] | Melting pt. [°C.] |
|---|---|---|---|---|---|---|---|---|---|
| 31 | C—CH₃ | N | C—C₂H₅ | O | CH₃ | C₂H₅ | B | 97 | 216 DMF |
| 32 | C—CH₃ | N | C—C₂H₅ | O | C₂H₅ | C₂H₅ | A | 43 | 132–134 Isopropanol |
| 33 | C—CH₃ | N | C—C₂H₅ | O | CH₃ | CH₂COCH₃ | B | 61 | 174–175 Ethanol |
| 34 | C—CH₃ | N | C—C₂H₅ | O | CH₃ | (CH₂)₃COCH₃ | B | 22 | 142–143 Ethanol |
| 35 | C—CH₃ | N | C—C₂H₅ | O | C₂H₅ | (CH₂)₂CH₂OH | B | 24 | 140–142 Isopropanol |
| 36 | C—CH₃ | N | C—C₂H₅ | O | C₂H₅ | (CH₂)₂CH₂SO₃H | B | 67 | 336–337 Isopropanol |
| 37 | C—CH₃ | N | C—C₂H₅ | O | CH₃ | (CH₂)₃COOH | B | 37 | 233–235 Isopropanol |
| 38 | C—CH₃ | N | C—C₂H₅ | O | C₂H₅ | (CH₂)₃COOH | B | 70 | 165 Ethanol |
| 39 | C—CH₃ | N | C—C₂H₅ | O | CH₃ | (CH₂)₃COOC₂H₅ | B | 94 | 140–141 DMF |
| 40 | C—CH₃ | N | C—C₂H₅ | O | C₂H₅ | (CH₂)₃COOC₂H₅ | B | 17 | 78 Ethanol |
| 41 | C—CH₃ | N | C—C₂H₅ | O | C₂H₅ | (CH₂)₃CON(CH₃)C₆H₁₁ | B | 11 | 133–135 Ethyl acetate |
| 42 | C—CH₃ | N | C—C₂H₅ | O | CH₃ | CH₂C₆H₅ | B | 70 | 165 DMF |
| 43 | C—CH₃ | N | C—C₂H₅ | O | C₂H₅ | CH₂C₆H₅ | B | 27 | 147–148 Isopropanol |
| 44 | C—CH₃ | N | C—C₂H₅ | O | CH₃ | CH₂C₆H₄(4-F) | B | 67 | 223 Isopropanol |
| 45 | C—CH₃ | N | C—C₂H₅ | O | C₂H₅ | CH₂C₆H₄(4-F) | B | 52 | 148–150 Isopropanol |
| 46 | C—CH₃ | N | C—C₂H₅ | O | CH₂C₆H₂(3,4,5-tri-OCH₃) | CH₂C₆H₂(3,4,5-tri-OCH₃) | A | 52 | 172–174 Cyclohexane |
| 47 | C—CH₃ | N | C—C₂H₅ | NH | H | CH₂C₆H₅ | B | 40 | 276–278 Ethanol |
| 48 | C—CH₃ | N | C—C₂H₅ | O | CH₃ |  | B | 9 | 173–175 Isopropanol |
| 49 | C—CH₃ | N | C—C₂H₅ | O | CH₃ | 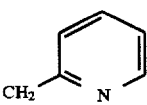 | B | 3 | 184–186 Ethanol |
| 50 | C—CH₃ | N | C—C₂H₅ | O | CH₃ | 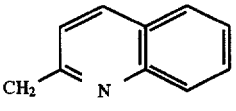 | B | 18 | 237–239 DMF |
| 51 | C—CH₃ | N | C—C₂H₅ | O | C₂H₅ | 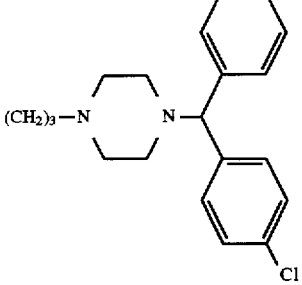 | A | 13 | 54–56 Cyclohexane |

What is claimed is:

1. Pyrido [3,2-e] pyrazinones of formula

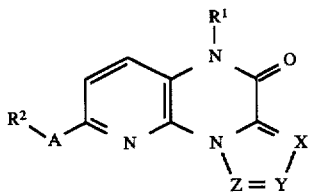

where

A represents $CH_2$, $NR^3$ or O;

X, Y, and Z represent N or $CR^4$, where at least one of X, Y and Z represents N;

$R^1$ represents $C_1$–$C_{10}$-alkyl (optionally branched) which is unsubstituted or substituted one or more times with hydroxy-, $C_1$–$C_6$-alkyloxy, $C_1$–$C_6$ alkenyloxy-, $C_1$–$C_6$ alkinyloxy-, aryl, aryloxy, heteroaryloxy, amino, mono-$C_1$–$C_6$-alkylamino, di-$C_1$–$C_6$-alkylamino, halogen, $NO_2$, CN, C=$OR^5$, or S(O)$_n$$R^6$ where n is 0–2, $C_1$–$C_{10}$-alkenyl (optionally branched) which is unsubstituted or substituted one or more times with hydroxy-, $C_1$–$C_6$-alkyloxy, $C_1$–$C_6$ alkenyloxy-, $C_1$–$C_6$ alkinyloxy-, aryl, aryloxy, heteroaryloxy, amino, mono-$C_1$–$C_6$-alkylamino, di-$C_1$–$C_6$-alkylamino, halogen, $NO_2$, CN, C=$OR^5$, or S(O)$_n$$R^6$ where n is 0–2, $C_1$–$C_{10}$-alkinyl (optionally branched) which is unsubstituted or substituted one or more times with hydroxy-, $C_1$–$C_6$-alkyloxy, $C_1$–$C_6$ alkenyloxy-, $C_1$–$C_6$ alkinyloxy-, aryl, aryloxy, heteroaryloxy, amino, mono-$C_1$–$C_6$-alkylamino, di-$C_1$–$C_6$-alkylamino, halogen, $NO_2$, CN, C=$OR^5$, or S(O)$_n$$R^6$ where n is 0–2, or $C_5$–$C_7$-cycloalkyl which is unsubstituted or substituted one or more times with hydroxy-, $C_1$–$C_6$-alkyloxy, $C_1$–$C_6$ alkenyloxy-, $C_1$–$C_6$ alkinyloxy-, aryl, aryloxy, heteroaryloxy, amino, mono-$C_1$–$C_6$-alkylamino, di-$C_1$–$C_6$-alkylamino, halogen, $NO_2$, CN, C=$OR^5$, or S(O)$_n$$R^6$ where n is 0–2;

$R^2$ represents

H, $C_1$–$C_{10}$-alkyl (optionally branched) which is unsubstituted or substituted one or more times with hydroxy-, $C_1$–$C_6$-alkyloxy, $C_1$–$C_6$ alkenyloxy-, $C_1$–$C_6$ alkinyloxy-, aryl, aryloxy, heteroaryloxy, amino, mono-$C_1$–$C_6$-alkylamino, di-$C_1$–$C_6$-alkylamino, halogen, $NO_2$, CN, C=$OR^5$, or S(O)$_n$$R^6$ where n is 0–3, $C_1$–$C_{10}$-alkenyl (optionally branched) which is unsubstituted or substituted one or more times with hydroxy-, $C_1$–$C_6$-alkyloxy, $C_1$–$C_6$ alkenyloxy-, $C_1$–$C_6$ alkinyloxy-, aryl, aryloxy, heteroaryloxy, amino, mono-$C_1$–$C_6$-alkylamino, di-$C_1$–$C_6$-alkylamino, halogen, $NO_2$, CN, C=$OR^5$, or S(O)$_n$$R^6$ where n is 0–2, $C_5$–$C_7$-alkinyl (optionally branched) which is unsubstituted or substituted one or more times with hydroxy-, $C_1$–$C_6$-alkyloxy, $C_1$–$C_6$ alkenyloxy-, $C_1$–$C_6$ alkinyloxy-, aryl, aryloxy, heteroaryloxy, amino, mono-$C_1$–$C_6$-alkylamino, di-$C_1$–$C_6$-alkylamino, halogen, $NO_2$, CN, C=$OR^5$, or S(O)$_n$$R^6$ where n is 0–2, $C_5$–$C_7$-cycloalkyl which is unsubstituted or substituted one or more times with hydroxy-, $C_1$–$C_6$-alkyloxy, $C_1$–$C_6$ alkenyloxy-, $C_1$–$C_6$ alkinyloxy-, aryl, aryloxy, heteroaryloxy, amino, mono-$C_1$–$C_6$-alkylamino, di-$C_1$–$C_6$-alkylamino, halogen, $NO_2$, CN, C=$OR^5$, or S(O)$_n$$R^6$ where n is 0–2, 4-(1-chlorophenyl-1-phenylmethyl)-1-piperazinylmethyl, quinolinylmethyl or pyridinylmethyl;

$R^3$ represents H or $C_1$–$C_6$-alkyl;

$R^4$ represents H, a branched or unbranched $C_1$–$C_6$-alkyl or a halogen;

$R^5$ represents H, branched or unbranched $C_1$–$C_6$-alkyl, phenyl, OH, branched or unbranched $C_1$–$C_6$ alkyloxy, aryloxy, amino, mono-$C_1$–$C_6$-alkylamino, or di-$C_1$–$C_6$-alkylamino;

$R^6$ represents H, $C_1$–$C_6$-alkyl, aryl, OH, $C_1$–$C_6$ alkyloxy, aryloxy, amino, mono-$C_1$–$C_6$-alkylamino, or di-$C_1$–$C_6$-alkylamino;

and physiologically acceptable salts thereof.

2. A process for the preparation of pyrido[3,2-e] pyrazinones of formula I comprising reacting compounds of formula

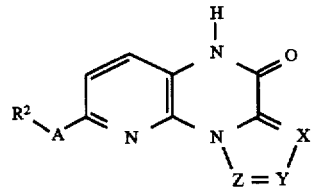

with $R^1$-Hal, wherein Hal represents a halogen and A, X, Y, Z, $R^1$, $R^2$, $R^3$, $R^4$, $R^5$ and $R^6$ have the meanings set forth in claim 1, in the presence of an inorganic or organic basic catalyst.

3. A process according to claim 2, wherein basic compounds of formula I are converted into salts.

4. A process according to claim 2, wherein acid compounds of formula I are converted into salts.

5. A process for the preparation of pyrido[3,2-e] pyrazinones of formula I where A, X, Y, Z, $R^1$, $R^2$, $R^3$, $R^4$, $R^5$ and $R^6$ have the meanings set forth in claim 1, comprising reacting compounds of formula

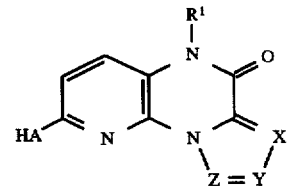

where A, X, Y, Z and $R^1$ have the meanings set forth in claim 1, with $R^2$-Hal, wherein Hal represents a halogen and $R^2$ has the meaning set forth in claim 1, in the presence of an inorganic or organic basic catalyst.

6. A process according to claim 5, wherein basic compounds of formula I are converted into salts.

7. A process according to claim 5, wherein acid compounds of formula I are converted into salts.

8. A method of treating asthma comprising administering a compound according to claim 1.

9. A method of treating allergy comprising administering a compound according to claim 1.

10. A medicament comprising at least one compound according to claim 1 and a conventional physiologically acceptable carrier or diluting agent.

11. A process for preparation of a medicament, said process comprising processing one or more compounds according to claim 1 with a conventional pharmaceutical carrier and/or a diluting agent to obtain a pharmaceutical formulation.

12. A method of treating asthma or allergy comprising administering a medicament according to claim 10.

* * * * *